United States Patent
Schwartz et al.

(10) Patent No.: US 7,991,469 B2
(45) Date of Patent: *Aug. 2, 2011

(54) PACING THERAPY FOR EXTENDING ATRIAL REFRACTORY PERIOD

(75) Inventors: Mark Schwartz, Redmond, WA (US); Jasbir Sra, Pewaukee, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1168 days.

This patent is subject to a terminal disclaimer.

(21) Appl. No.: 11/687,776

(22) Filed: Mar. 19, 2007

(65) Prior Publication Data

US 2007/0167987 A1 Jul. 19, 2007

Related U.S. Application Data

(63) Continuation of application No. 10/302,747, filed on Nov. 22, 2002, now Pat. No. 7,203,538.

(51) Int. Cl.
*A61N 1/00* (2006.01)
(52) U.S. Cl. .............................. 607/9; 607/14
(58) Field of Classification Search .................. 607/4–6, 607/9, 13, 14, 15
See application file for complete search history.

(56) References Cited

U.S. PATENT DOCUMENTS

| | | | |
|---|---|---|---|
| 4,554,922 A | 11/1985 | Prystowsky et al. | |
| 5,334,221 A | 8/1994 | Bardy | |
| 5,344,221 A | 9/1994 | MacWilliam | |
| 5,645,569 A | 7/1997 | Ayers | |
| 5,676,687 A | 10/1997 | Ayers | |
| 5,741,311 A | 4/1998 | Mc Venes et al. | |
| 6,377,852 B1 | 4/2002 | Bornzin et al. | |
| 6,701,187 B1 | 3/2004 | Bornzin et al. | |
| 7,062,318 B2 | 6/2006 | Ben-Haim et al. | |
| 7,203,538 B2 * | 4/2007 | Schwartz et al. | 607/4 |
| 2001/0018600 A1 | 8/2001 | Plicchi et al. | |

FOREIGN PATENT DOCUMENTS

| | | |
|---|---|---|
| EP | 0811399 A2 | 12/1997 |
| EP | 1118352 A2 | 7/2001 |
| JP | 2000-502931 | 3/2000 |
| WO | WO-97/25098 A1 | 7/1997 |
| WO | WO-9727797 A2 | 8/1997 |

OTHER PUBLICATIONS

"U.S. Appl. No. 10/302,747, Non-Final Office Action mailed Jul. 6, 2006", 4 pgs.
"U.S. Appl. No. 10/302,747, Notice of Allowance mailed Nov. 28, 2006", 4 pgs.
"U.S. Appl. No. 10/302,747, Response filed Apr. 10, 2006 to Restriction Requirement mailed Mar. 8, 2006", 7 pgs.
"U.S. Appl. No. 10/302,747, Response filed Nov. 6, 2006 to Non-Final Office Action mailed Jul. 6, 2006", 9 pgs.

(Continued)

*Primary Examiner* — Mark W Bockelman
(74) *Attorney, Agent, or Firm* — Schwegman, Lundberg & Woessner, P.A.

(57) ABSTRACT

A device and method are presented for prolonging the atrial effective refractory period with pacing therapy. Such refractory period prolongation renders the atrial tissue less susceptible to the onset of atrial fibrillation. A particularly useful application is during the period after application of electrical therapy to the atria to terminate an episode of atrial fibrillation.

20 Claims, 4 Drawing Sheets

OTHER PUBLICATIONS

"U.S. Appl. No. 10/302,747, Restriction Requirement mailed Mar. 8, 2006", 5 pgs.

"European Application Serial No. 03769000.5, Communication dated Mar. 9, 2006", 2 pgs.

"European Application Serial No. 03769000.5, Response filed Jul. 10, 2006 to Communication dated Mar. 9, 2006", 1 pg.

"International Application Serial No. PCT/US03/37155, International Search Report mailed May 6, 2004", 5 pgs.

"Japanese Application Serial No. 2004-555514, Office Action mailed Aug. 31, 2009", (w/ partial translation), 4 pgs.

"Japanese Application Serial No. 2004-555514, Response filed Nov. 24, 2009 to Office Action mailed Aug. 31, 2009", (w/ English Translation of Amended Claims), 37 pgs.

"Japanese Application Serial No. 2004-555514, Office Action mailed on Feb. 8, 2010", (partial English translation), 2 pgs.

Krum, David, et al., "Pacing to Prevent Atrial Fibrillaation: The Effect of High Frequency Atrial Burst Pacing Algorithms on Atrial EPR", *Oral Presentation presented at PACE, North American Society of Pacing and Electrophysiology*, May 17-20, 2000, Washington Convention Center, Washington, D.C., USA, 10.

Krum, David, et al., "Pacing to Prevent Atrial Fibrillation: The Effect of High Frequency Atrial Burst Pacing Algorithms on Atrial ERP", *PACE*, vol. 23, No. 4, Part II, Apr. 2000, 582.

Wijffels, Maurits C., et al., "Atrial Fibrillation Begets Atrial Fibrillation: A Study in Awake Chronically Instrumented Goats", *Circulation*, vol. 92, No. 7, (Oct. 1, 1995), 1954-1968.

\* cited by examiner

PACING THERAPY FOR EXTENDING ATRIAL REFRACTORY PERIOD

CROSS REFERENCE TO RELATED APPLICATIONS

This application is a continuation of U.S. patent application Ser. No. 10/302,747, filed on Nov. 22, 2002, now issues as U.S. Pat. No. 7,203,538, the specification of which is incorporated herein by reference.

FIELD OF THE INVENTION

This invention pertains to cardiac rhythm management devices and methods for operating such devices.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include ventricular tachycardia, ventricular fibrillation, atrial tachycardia, atrial flutter, and atrial fibrillation. Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

An electrical shock applied to a heart chamber can be used to terminate most tachyarrhythmias. The electric shock terminates the tachyarrhythmia by depolarizing all of the myocardium simultaneously and rendering it refractory. A class of cardiac rhythm management devices known as an implantable cardioverter/defibrillator (ICD) provides this kind of therapy by delivering a shock pulse to the heart when the device detects fibrillation. ICDs can be designed to treat either atrial or ventricular tachyarrhythmias, or both, and may also incorporate cardiac pacing functionality for delivering either bradycardia pacing or anti-tachycardia pacing (ATP). In ATP, the heart is competitively paced with one or more pacing pulses in an effort to interrupt the reentrant circuit causing the tachycardia.

The most dangerous tachyarrhythmias are ventricular tachycardia and ventricular fibrillation, and ICDs have most commonly been applied in the treatment of those conditions. ICDs are also capable, however, of detecting atrial fibrillation and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy. (As the term is used herein, atrial fibrillation should also be taken to include atrial flutter, which although clinically distinct, has similar consequences and may be treated similarly.)

Although atrial fibrillation can be successfully treated with electrical therapy from an implantable cardiac rhythm management device, it would be preferable to prevent an episode of atrial fibrillation from occurring. Another problem associated with defibrillation shock therapy is early recurrence of atrial fibrillation or ERAF. ERAF is defined as the recurrence of atrial fibrillation within a few minutes after successful cardioversion with atrial shock therapy. Certain patients are more prone than others to experience ERAF, and these patients may experience difficulty with repeated atrial defibrillation therapy. Reducing the incidence of ERAF would improve the efficacy of atrial defibrillation by electrical therapy and expand the population of patients for whom it is an acceptable therapy option.

SUMMARY

The length of the atrial effective refractory period (AERP) is one factor that determines the susceptibility of the atria to the onset of atrial fibrillation. By pacing the atria and delivering one or more non-excitatory stimulation pulses during the refractory period following each pace, the atrial effective refractory period can be extended. An implantable cardiac rhythm management device can be configured and programmed to deliver such AERP-extension pacing for a specified period of time automatically in response to a detected condition or in response to a command delivered by an external programmer. The non-excitatory stimulation pulses may be delivered in conjunction with any bradycardia atrial pacing mode. The bradycardia pacing mode may also employ overdrive pacing of the atria to increase the frequency of pacing and of non-excitatory stimulation for lengthening the AERP. The atrial sites where the pacing pulses and non-excitatory stimuli are delivered may be the same or different. One particularly useful application of AERP-extension pacing is to lessen the occurrence of early recurrence of atrial fibrillation following delivery of electrical stimulation therapy to the atria in the form of either an atrial defibrillation shock or atrial anti-tachycardia pacing. AERP-extension pacing may also be delivered periodically during normal pacing as a preventative measure.

DETAILED DESCRIPTION

Atrial fibrillation is a condition in which the electrical activity of the atrium becomes very rapid and disorganized. Instead of the sinus node providing the normal excitation to the atrium, rapid circulating waves of abnormal waves of depolarization continuously stimulate the atrium, resulting in a rapid atrial rate that can exceed 400 beats per minute. Research has shown that a combination of slow intra-atrial conduction and a short atrial refractory period in the atrial myocardial substrate contribute to conditions necessary to sustain the multiple re-entrant waves of depolarization responsible for atrial fibrillation.

Figure 1:
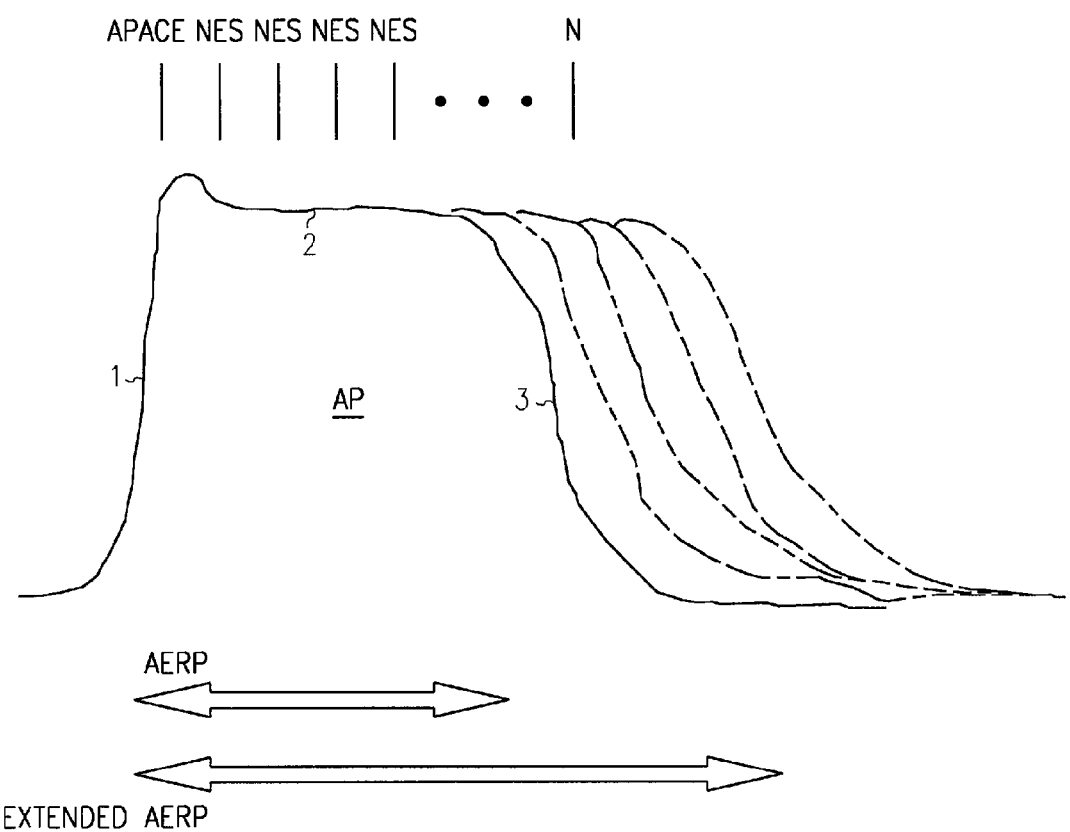
FIG. 1 is an atrial action potential waveform.

Like all excitable tissue, cardiac muscle cells are capable of generating a rapid change in transmembrane electrical potential, called an action potential, when the resting potential of the cell is depolarized to a threshold potential. The resulting depolarization then initiates the intracellular reactions responsible for mechanical contraction and propagates to adjacent cells as a wave of excitation that spreads throughout the myocardium. FIG. 1 illustrates an action potential AP of an atrial muscle cell as might be recorded from an intracellular electrode when the cell is excited due to either conduction of excitation from adjacent tissue or application of a pacing pulse. The action potential may be divided into an excitation phase 1 where the cell rapidly depolarizes, a plateau phase 2 where the depolarized state is maintained, and a repolarization phase 3 where the cell returns to its resting membrane potential. Myocardial cells are refractory to excitation for a period of time after being depolarized when no further action potentials can be generated. The refractory period can be subdivided into an absolute refractory period during which no stimulus is capable of exciting the cells and causing an action potential, and a relative refractory period during which a larger than normal stimulus is required to generate an action potential. The combination of the absolute and relative refractory periods in an atrial muscle cell is referred to as the atrial effective refractory period (AERP). As shown in FIG. 1, the duration of the AERP corresponds roughly to the duration of the action potential.

The refractoriness of myocardial cells can be prolonged if the cells are stimulated during the refractory period with non-excitatory electrical pulses which can be either below or above the normal threshold potential for initiating an action potential. FIG. 1 shows an atrial pacing pulse A-pace that causes the action potential AP and which is then followed by a number n of non-excitatory stimulus pulses NES delivered during the plateau phase when the atrial cell is absolutely refractory. Since the cell is absolutely refractory, the non-excitatory stimulus pulses can be either subthreshold or suprathreshold. As shown in the figure, the application of the non-excitatory stimulus pulses causes extension of the AERP, effectively changing the atrial substrate and thus reducing the susceptibility of the tissue to fibrillation.

As described below, a cardiac rhythm management device can be configured to deliver atrial pacing together with non-excitatory stimuli during the refractory period after a pace to thereby extend the AERP. Such AERP-extension pacing may be employed to lessen the probability that atrial fibrillation will occur whenever conditions warrant, such as during the period following the application of an atrial defibrillation shock or atrial ATP therapy.

1. Hardware Platform

Cardiac rhythm management devices are implantable devices that provide electrical stimulation to selected chambers of the heart in order to treat disorders of cardiac rhythm and include pacemakers and implantable cardioverter/defibrillators. Such devices are usually implanted subcutaneously on the patient's chest, and are connected to an electrode for each stimulated or sensed heart chamber by leads threaded through the vessels of the upper venous system into the heart. A pacemaker is a cardiac rhythm management device that paces the heart with timed pacing pulses. The term "pacemaker" as used herein should be taken to mean any device with a pacing functionality, such as an implantable cardioverter/defibrillator with a pacemaker incorporated therein.

In the description that follows, a microprocessor-based cardiac rhythm management device will be referred to as incorporating the system and method that is the present invention. In the embodiment to be described, the invention is implemented with a controller made up of a microprocessor executing programmed instructions in memory. It should be appreciated, however, that certain functions of a cardiac rhythm management device could be controlled by custom logic circuitry either in addition to or instead of a programmed microprocessor. As used herein, the terms "circuitry" or "programmed controller" should be taken to encompass either custom circuitry (i.e., dedicated hardware) or processor-executable instructions contained in a memory along with associated circuit elements.

Figure 2:
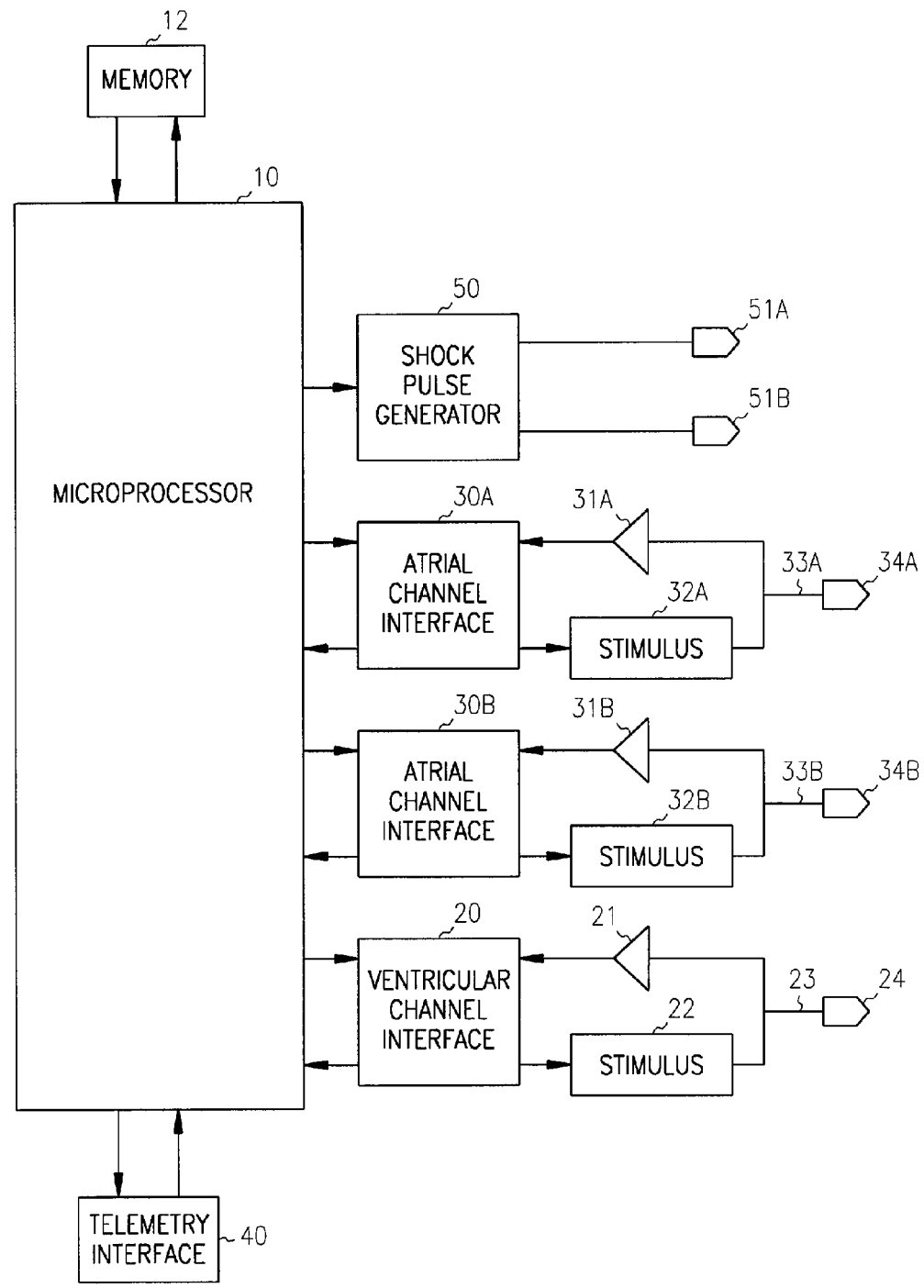
FIG. 2 is a block diagram of an exemplary cardiac rhythm management device.

FIG. 2 shows a system diagram of a microprocessor-based cardiac rhythm management device with pacing functionality that is suitable for delivering therapy to treat AF and to extend the atrial effective refractory period. The controller 10 of the device is a microprocessor that communicates with a memory 12 via a bidirectional data bus. The memory 12 may comprise, for example, a ROM (read-only memory) for program storage and a RAM (random-access memory) for data storage. The device has atrial sensing and pacing channels comprising electrodes 34a-b, leads 33a-b, sensing amplifiers 31a-b, pulse generators 32a-b, and atrial channel interfaces 30a-b which communicate bidirectionally with microprocessor 10. A ventricular sensing/pacing channel comprising electrode 24, lead 23, sensing amplifier 21, pulse generator 22, and ventricular channel interface 20 is also provided. The device may also have additional channels for sensing and/or pacing additional atrial sites or the ventricles. In the illustrated device, a single electrode is used for sensing and pacing in each channel, known as a unipolar lead. Other embodiments may employ bipolar leads that include two electrodes for outputting a pacing pulse and/or sensing intrinsic activity. The channel interfaces 30a-b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A shock pulse generator 50 is interfaced to the controller for delivering atrial defibrillation shock pulses via a pair of shock electrodes 51a and 51b placed in proximity to an atrial region. A telemetry interface 40 allows for communicating with an external programmer.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when an electrogram signal (i.e., a voltage sensed by an electrode representing cardiac electrical activity) generated by a particular channel exceeds a specified detection threshold. A chamber sense may be either an atrial sense or a ventricular sense depending on whether it occurs in the atrial or ventricular sensing channel. Pacing algorithms used in particular pacing modes employ such senses to trigger or inhibit pacing.

The controller may also determine the intrinsic rate of the atria and/or ventricles by measuring the interval between successive senses. Atrial arrhythmias such as fibrillation can be detected in this manner using a rate-based criterion. The device may be configured to deliver electrical stimulation therapy to the atria when an atrial tachyarrhythmia is detected such as a defibrillation shock or atrial anti-tachycardia pacing. Upon such detection of atrial fibrillation, for example, the controller may be programmed to cause the delivery of a defibrillation shock to the atria. If subsequent sensing determines that the atrial fibrillation persists, the device may repeat the shock a specified number of times successful termination of the fibrillation is achieved. The device terminates atrial fibrillation by delivering a shock pulse to the atria, but the resulting depolarization also spreads to the ventricles. There is thus a risk that such an atrial shock pulse can actually induce ventricular fibrillation, a condition much worse than atrial fibrillation. The ventricles are especially vulnerable to induction of fibrillation by a depolarizing shock delivered at a time too near the end of the preceding ventricular contraction (i.e., close to the T wave on an EKG). The risk of inducing ventricular fibrillation can be reduced by delaying the delivery of an atrial shock pulse until the intrinsic ventricular rhythm is below a specified maximum rate and then delivering the shock synchronously with a sensed ventricular depolarization or R wave. The device may also have a shock pulse generator and shock electrode pair for delivering defibrillation shocks to the ventricles.

2. Pacing Modes

Bradycardia pacing modes refer to pacing algorithms used to pace the atria and/or ventricles in a manner that enforces a certain minimum heart rate. Such modes are generally designated by a letter code of three positions where each letter in the code refers to a specific function of the pacemaker. Pacemakers can enforce a minimum heart rate either asynchronously or synchronously. In asynchronous pacing, the heart is paced at a fixed rate irrespective of intrinsic cardiac activity. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval can be defined between ventricular events so as to be restarted with each ventricular sense or pace. A pacemaker can also be configured to pace the atria on an inhibited demand basis. An atrial escape interval is then defined as the maximum time interval in which an atrial sense must be detected after a ventricular sense or pace before an atrial pace will be delivered.

Pacing protocols for ATP therapy can generally be divided into two classes: those that deliver one or more pulses in timed relation to detected depolarizations and those that deliver a continuous pulse train for a specified time beginning after a detected depolarization. Both types of ATP protocols attempt to block the reentrant depolarization wavefront causing the tachycardia with a second depolarizing wavefront produced by a pacing pulse. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses.

3. Device Configuration

Figure 3:
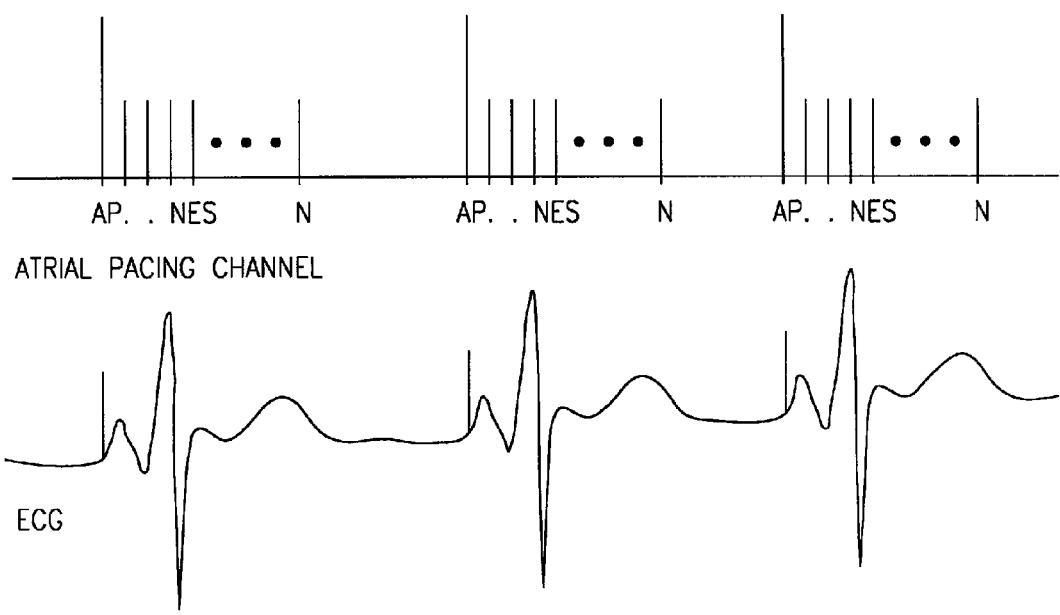
FIG. 3 shows the pacing events during AERP-extension pacing in relation to an ECG.

A device such as illustrated in FIG. 2 may be configured to deliver atrial pacing with atrial effective refractory period extension in a number of ways. In an exemplary dual-site configuration, the electrode of a first pacing channel is disposed in the right atrium for pacing that atrium, and the electrode of a second pacing channel is placed near the left atrium via the coronary sinus for delivery of the non-excitatory stimuli. Other configurations may use an atrial pacing channel and one or more dedicated stimulation channels where the pacing and one or more non-excitatory stimulus electrodes are placed at multiple atrial sites. Other devices may use the same pacing channel and electrode for delivering both pacing and non-excitatory pulses in a single-site configuration. With either a single-site or multiple-site configuration, the controller of the device is programmed with an AERP-extension mode that paces an atrium via the pacing channel using a bradycardia pacing mode and delivers one or more non-excitatory stimuli after a pacing pulse as described above. FIG. 3 shows an example of events in the pacing channel or channels PC in relation to an ECG. An atrial pacing pulse AP is followed by n non-excitatory stimulation pulses NSP, where the pulses NSP are delivered during the atrial refractory period and hence their amplitudes may be either above or below the threshold voltage needed to excite the atrial tissue. The atrial refractory period is defined in the programming of the device as a specified time period following the atrial pace. The atrial refractory period may be individually defined for a particular patient or selected as a nominal value representing the refractory period of a typical atrial fiber (e.g., 150 ms).

4. Overdrive Pacing

The bradycardia pacing mode employed with the AERP-extension mode is preferably an inhibited demand mode where atrial senses inhibit atrial paces. Since the non-excitatory stimuli that extend the refractory period are only output during paced beats, it may be desirable to increase the frequency of atrial pacing by decreasing the atrial escape interval so that the pacing rate is greater than the intrinsic heart rate, termed overdrive pacing. Such an overdrive atrial pacing mode may be implemented by dynamic adjusting the atrial escape interval so that the interval is decreased when an atrial sense is detected and slowly increased after each paced beat.

Figure 4A:
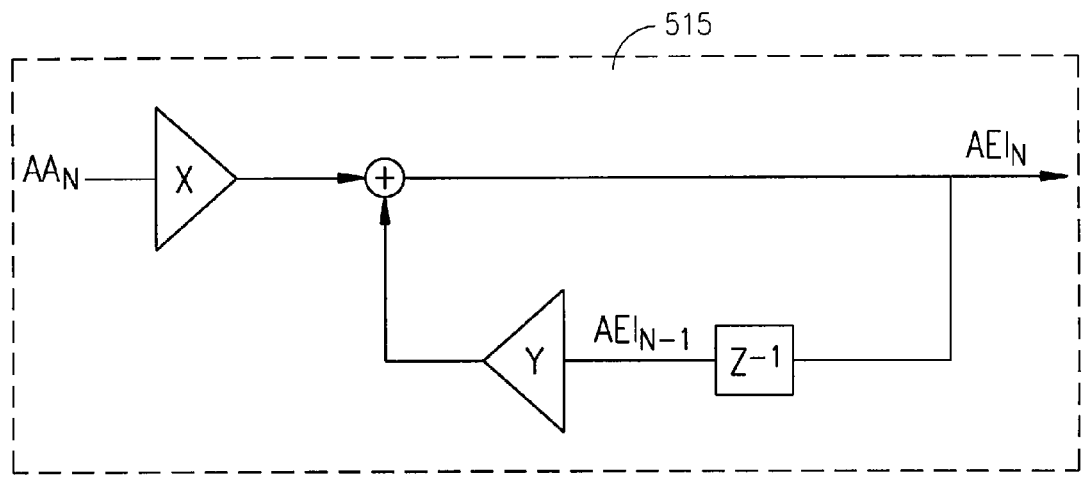
FIGS. 4A and 4B illustrate an exemplary system for overdrive pacing of the atria.
Figure 4B:
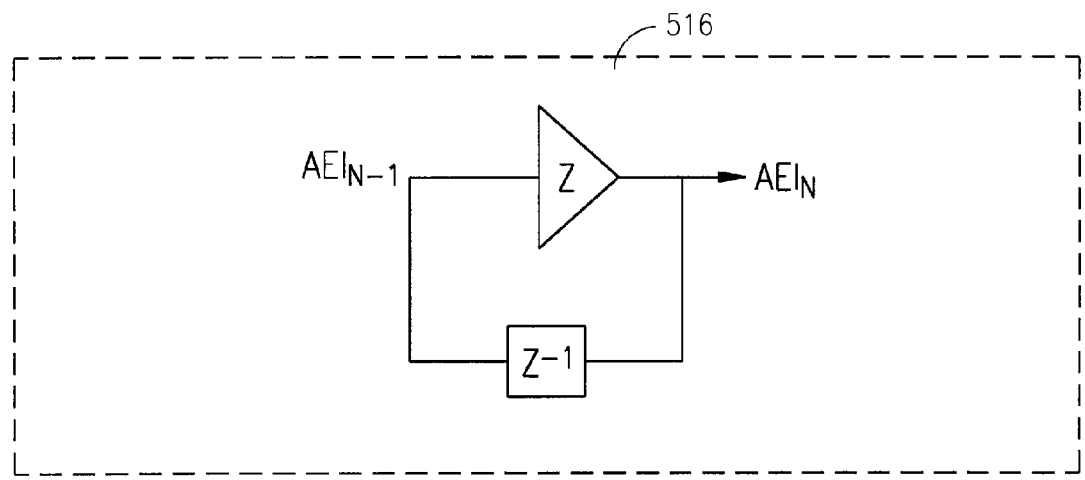

In one embodiment of atrial overdrive pacing, the atrial escape interval is adjusted to decrease toward a programmed minimum value by measuring an A-A interval (defined as the time interval between the atrial sense and the preceding atrial sense or pace) when an atrial sense occurs and then computing an updated atrial escape interval based upon the measured A-A interval. When an atrial pace is delivered, on the other hand, the atrial escape interval is made to slowly increase so that the atrial pacing rate decays toward its programmed base value. FIGS. 4A and 4B show an exemplary implementation of an overdrive pacing system made up of a pair of filters 515 and 516 which may be implemented as software executed by the controller 10 (a.k.a. firmware) and/or with discrete components. Filter 515 is employed to compute the updated atrial escape interval when an atrial sense occurs, and filter 516 is used when an atrial pace is delivered. When an atrial sense occurs, the measured A-A interval is input to a recursive digital filter 515 whose output is the updated atrial escape interval. The filter 515 multiplies the measured A-A interval by a filter coefficient A and then adds the result to the previous value of the output (i.e., the present atrial escape interval) multiplied by a filter coefficient B. The operation of the filter is thus described by $AEI_n = X(AA_n) + Y(AEI_{n-1})$, where X and Y are selected coefficients, $AA_n$ is the most recent A-A interval duration, and $AEI_{n-1}$ is the previous value of the atrial escape interval. The filter thus causes the value of the atrial escape interval to move toward the present A-A interval multiplied by a scaling factor at a rate determined by the filter coefficients. When an atrial pace is delivered due to expiration of the atrial escape interval without an atrial sense, filter 516 multiplies the present atrial escape interval by a filter coefficient Z so that $AEI_n = Z(AEI_{n-1})$. To provide stable operation, the coefficient Z must be set to a value greater than 1. Filter 516 then causes the atrial escape interval to increase in an exponential manner with each pace as successive values of the escape interval are input to the filter up to a value corresponding to the base atrial escape interval. In order to overdrive the atria, the coefficients of filters 515 and 516 are selected so that the atrial escape interval decreases rapidly toward a value less than the present A-A interval when an atrial sense occurs and increases slowly toward a programmed base value when a pace is delivered.

5. Initiation of AERP-extension Pacing

The controller may be programmed to enter the AERP-extension mode for a specified time period either upon command from an external programmer, periodically or at other specified times during normal operation, or in response to sensed events. One particular situation where AERP-extension pacing may be especially beneficial is in the period following an atrial defibrillation shock. It has been found that the atria are in a supervulnerable period lasting approximately one minute immediately following an atrial defibrillation shock. During this time, the atrial effective refractory period is shortened from its value during the atrial fibrillation. This condition predisposes the patient to post-shock re-initiation of the atrial fibrillation, commonly referred to as early recurrence of atrial fibrillation or ERAF. To deal with this situation, the device can be programmed so that, upon detection of atrial fibrillation, an atrial defibrillation shock is delivered to terminate the fibrillation followed by AERP-extension pacing for a specified time period. The device may also be programmed to deliver AERP-extension pacing for a specified time following delivery of atrial anti-tachycardia pacing.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   an atrial sensing channel for sensing atrial electrical activity;
   an atrial pacing channel for delivering atrial pacing pulses;
   a controller programmed to periodically switch to an atrial effective refractory period extension mode that includes:
   delivering atrial pacing pulses upon expiration of an atrial escape interval that is dynamically adjusted by decreasing the escape interval when an atrial sense is detected and increasing the escape interval after an atrial pace; and,
   delivering one or more non-excitatory stimulation pulses to an atrium during an atrial refractory period after an atrial pacing pulse.

2. The device of claim 1 wherein the non-excitatory stimulation pulses are of lesser amplitude than the atrial pacing pulses.

3. The device of claim 1 wherein the non-excitatory stimulation pulses are of equal or greater amplitude than the atrial pacing pulses.

4. The device of claim 1 wherein the non-excitatory stimulation pulses are delivered through the atrial pacing channel.

5. The device of claim 1 further comprising an atrial stimulation channel for delivering the non-excitatory stimulation pulses.

6. The device of claim 1 further comprising a plurality of atrial stimulation channels and wherein the controller is programmed to deliver non-excitatory atrial stimulation pulses through the plurality of atrial stimulation channels after an atrial pace during the specified period of time.

7. The device of claim 1 wherein the controller is programmed to:
   measure an A-A interval for each atrial sense, defined as the time interval between the atrial sense and the preceding atrial sense or pace;
   compute an updated atrial escape interval $AEI_n$ after an atrial sense as:

$$AEI_n = X(AA_n) + Y(AEI_{n-1})$$

where X and Y are selected coefficients, $AA_n$ is the most recent A-A interval duration, and $AEI_{n-1}$ is the previous value of the atrial escape interval; and,
   compute an updated atrial escape interval after an atrial pace as:

$$AEI_n = Z(AEI_{n-1})$$

where Z is a specified coefficient.

8. A method, comprising:
   delivering atrial pacing pulses to an atrial pacing site in accordance with a pacing mode for a specified period of time in which atrial pacing pulses are delivered upon expiration of an atrial escape interval that is dynamically adjusted by decreasing the escape interval when an atrial sense is detected and increasing the escape interval after an atrial pace; and,
   delivering one or more non-excitatory stimulation pulses to an atrial stimulation site during the atrial refractory period after an atrial pacing pulse.

9. The method of claim 8 wherein the non-excitatory stimulation pulses are of lesser amplitude than the atrial pacing pulses.

10. The method of claim 8 wherein the non-excitatory stimulation pulses are of equal or greater amplitude than the atrial pacing pulses.

11. The method of claim 8 further comprising delivering the non-excitatory stimulation pulses to an atrial stimulation site different from the atrial pacing site.

12. The method of claim 8 wherein the atrial pacing site is in one atrium and the atrial stimulation site is in the contralateral atrium.

13. The method of claim 8 further comprising delivering non-excitatory atrial stimulation pulses to a plurality of atrial stimulation sites after an atrial pace during the specified period of time.

14. The method of claim 8 further comprising:
   measuring an A-A interval for each atrial sense, defined as the time interval between the atrial sense and the preceding atrial sense or pace;
   computing an updated atrial escape interval $AEI_n$ after an atrial sense as:

$$AEI_n = X(AA_n) + Y(AEI_{n-1})$$

where X and Y are selected coefficients, $AA_n$ is the most recent A-A interval duration, and $AEI_{n-1}$ is the previous value of the atrial escape interval; and,
   computing an updated atrial escape interval after an atrial pace as:

$$AEI_n = Z(AEI_{n-1})$$

where Z is a specified coefficient.

15. A cardiac rhythm management device, comprising:
   means for delivering atrial pacing pulses to an atrial pacing site in accordance with a pacing mode for a specified period of time in which atrial pacing pulses are delivered upon expiration of an atrial escape interval that is dynamically adjusted by decreasing the escape interval when an atrial sense is detected and increasing the escape interval after an atrial pace; and,
   means for delivering one or more non-excitatory stimulation pulses to an atrial stimulation site during the atrial refractory period after each atrial pacing pulse during the specified period of time.

16. The device of claim 15 wherein the non-excitatory stimulation pulses are of lesser amplitude than the atrial pacing pulses.

17. The device of claim 15 wherein the non-excitatory stimulation pulses are of equal or greater amplitude than the atrial pacing pulses.

18. The device of claim 15 further comprising means for delivering the non-excitatory stimulation pulses to an atrial stimulation site different from the atrial pacing site.

19. The device of claim 15 wherein the atrial pacing site is in one atrium and the atrial stimulation site is in the contralateral atrium.

20. The device of claim 15 further comprising means for delivering non-excitatory atrial stimulation pulses to a plurality of atrial stimulation sites after an atrial pace during the specified period of time.

* * * * *